(12) United States Patent
Zeng et al.

(10) Patent No.: US 8,731,266 B2
(45) Date of Patent: May 20, 2014

(54) METHOD AND SYSTEM FOR CORRECTING ARTIFACTS IN IMAGE RECONSTRUCTION

(75) Inventors: Kai Zeng, Niskayuna, NY (US); Bruno Kristiaan Bernard DeMan, Clifton Park, NY (US); Jean-Baptiste Thibault, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 1188 days.

(21) Appl. No.: 12/640,936

(22) Filed: Dec. 17, 2009

(65) Prior Publication Data

US 2011/0150305 A1    Jun. 23, 2011

(51) Int. Cl.
*A61B 6/03* (2006.01)
(52) U.S. Cl.
CPC ........................................ *A61B 6/03* (2013.01)
USPC .......................................................... 382/131
(58) Field of Classification Search
CPC ....................................................... A61B 6/03
USPC .......................................................... 382/131
See application file for complete search history.

(56) References Cited

U.S. PATENT DOCUMENTS

| | | | |
|---|---|---|---|
| 6,768,782 B1 | 7/2004 | Hsieh et al. |
| 6,907,102 B1 | 6/2005 | Sauer et al. |
| 6,944,260 B2 | 9/2005 | Hsieh et al. |
| 7,215,731 B1 | 5/2007 | Basu et al. |
| 7,251,306 B2 | 7/2007 | Sauer et al. |
| 7,254,209 B2 | 8/2007 | Zhao et al. |
| 7,272,205 B2 | 9/2007 | Thibault et al. |
| 7,308,071 B2 | 12/2007 | Bouman et al. |
| 7,327,822 B2 | 2/2008 | Sauer et al. |
| 7,362,843 B2 | 4/2008 | Basu et al. |
| 7,379,527 B2 | 5/2008 | Wu et al. |
| 7,386,088 B2 | 6/2008 | DeMan et al. |
| 7,440,602 B2 | 10/2008 | Hsieh et al. |
| 7,551,708 B2 | 6/2009 | Basu et al. |
| 7,583,780 B2 | 9/2009 | Hsieh et al. |
| 2006/0072800 A1 | 4/2006 | DeMan et al. |
| 2007/0058771 A1 | 3/2007 | Sauer et al. |
| 2007/0116343 A1 | 5/2007 | Sauer et al. |
| 2007/0205367 A1 | 9/2007 | DeMan et al. |
| 2007/0297656 A1 | 12/2007 | DeMan et al. |
| 2008/0063135 A1 | 3/2008 | DeMan et al. |
| 2008/0118020 A1 | 5/2008 | Thibault et al. |
| 2008/0304726 A1 | 12/2008 | Fessler et al. |
| 2009/0110259 A1 | 4/2009 | Yin et al. |
| 2009/0190814 A1 | 7/2009 | Bouman et al. |
| 2009/0232269 A1 | 9/2009 | Hsieh et al. |
| 2009/0238427 A1 | 9/2009 | Hsieh et al. |

OTHER PUBLICATIONS

Manzke et al., Helical Cardiac cone beam CT reconstruction with large area detectors: a simulation study, 2005, Physics in Medicine and Biology, vol. 50, pp. 1547-1568.*

Beque, Dirk et al.; "Iterative Reconstruction for Multi-Source Inverse Geometry CT: a Feasibility Study"; Proc. SPIE, vol. 6510, 65105Y (2007).

Tam, K.C. et al.; "Exact Cone-Beam CT With a Spiral Scan"; Phys. Med. Biol., vol. 43, pp. 1015-1024, 1998.

* cited by examiner

*Primary Examiner* — Toan Ton
*Assistant Examiner* — John Corbett
(74) *Attorney, Agent, or Firm* — Fletcher Yoder, P.C.

(57) ABSTRACT

Methods and systems are provided for correcting artifacts in iterative reconstruction processes. In certain embodiments, weighting schemes may be applied such that less than all of the available scan or projection data is utilized in the iterative reconstruction. In this manner, inconsistencies in the data undergoing reconstruction may be reduced.

16 Claims, 6 Drawing Sheets

METHOD AND SYSTEM FOR CORRECTING ARTIFACTS IN IMAGE RECONSTRUCTION

BACKGROUND OF THE INVENTION

The subject matter disclosed herein relates to non-invasive imaging and, in particular, to correcting or reducing artifacts in the image reconstruction process.

In the fields of medical imaging, animal imaging, quality control and security screening, non-invasive imaging techniques have gained importance due to benefits that include unobtrusiveness, convenience, and speed. In medical and research contexts, non-invasive imaging techniques are used to image organs or tissues beneath the surface of the skin. Similarly, in industrial or quality control (QC) contexts, non-invasive imaging techniques are used to examine parts or items for hidden defects that may not be evident from an external examination. In security screening, non-invasive imaging techniques are typically used to examine the contents of containers (e.g., packages, bags, or luggage) without opening the containers and/or to screen individuals entering or leaving a secure location.

A number of non-invasive imaging modalities exist today. A particular modality may be selected based upon the imaging context, such as the organ or tissue to be imaged, the spatial and/or temporal resolution desired, or upon whether structural or functional characteristics are of interest. One type of imaging modality is computed tomography (CT) in which X-ray attenuation data is collected at different angular positions relative to the subject or object undergoing imaging. The collected data is reconstructed to generate three-dimensional representations of the subject or object undergoing imaging, including those internal structures not typically visible in an external examination. One technique by which image data may be reconstructed is iterative reconstruction, which may be utilized when it is desired to optimize image quality and minimize patient dose.

However, the iterative reconstruction process may be susceptible to various undesired image artifacts in the generated image. These artifacts may arise from a number of sources, including motion of or within the subject being imaged, data inconsistencies introduced by the scan protocol, and/or data inconsistencies introduced by the reconstruction technique. The artifacts may degrade the image quality and/or reduce the usefulness of the images. However, even if the artifacts do not reduce the usefulness of the images, their presence is still typically undesirable as they detract from the image quality. In some instances, iterative reconstruction methods may be as or more susceptible to such artifacts than direct reconstruction techniques, such as filtered backprojection (FBP).

BRIEF DESCRIPTION OF THE INVENTION

In an embodiment, an image reconstruction method is provided. In accordance with this embodiment, one or more sets of scan data acquired using a computed tomography system are accessed. A voxel-dependent angular weighting function corresponding to the one or more sets of scan data is computed. The respective weighting function is used to iteratively compute a set of images from the sets of scan data, such that the angular range of the data contributing to each voxel is made more uniform and/or the angular range is narrowed for one or more voxels.

In one embodiment, an image reconstruction method is provided. In accordance with this embodiment, one or more sets of projection data acquired using a computed tomography system are accessed. A detector-channel dependent projection-domain weighting corresponding to the one or more sets of projection data is computed such that the contribution from one or more detector regions is reduced. The detector-channel dependent projection-domain weighting is applied to iteratively reconstruct one or more images In another embodiment, an image reconstruction method is provided. In accordance with this embodiment, inconsistent regions of a sinogram used in a model-based iterative reconstruction are identified. The inconsistent regions are determined based on the magnitude of an error sinogram after a number of iterations. A filtered backprojection (FBP) is performed to reconstruct an FBP image. The FBP image is reprojected to generate all or part of a reprojected sinogram. Portions of the reprojected sinogram corresponding to the identified inconsistent regions are substituted in the sinogram to generate a blended sinogram. The blended sinogram is iteratively reconstructed to reconstruct one or more images

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

The embodiments discussed below describe various approaches for reducing artifacts using iterative image reconstruction techniques to reconstruct tomographic image data. In general, these approaches reduce artifacts that are attributable to inconsistencies present in the data in model-based statistical iterative reconstruction (MBIR). Such inconsistencies may be present due to motion of the subject or motion within the region undergoing imaging and/or due to geometric constraints associated with the scan protocol. Before a detailed discussion of the system and methods are described in accordance with various embodiments of the present technique, it may be beneficial to discuss embodiments of imaging systems that may be suitable for performing the methods described herein.

Figure 1:
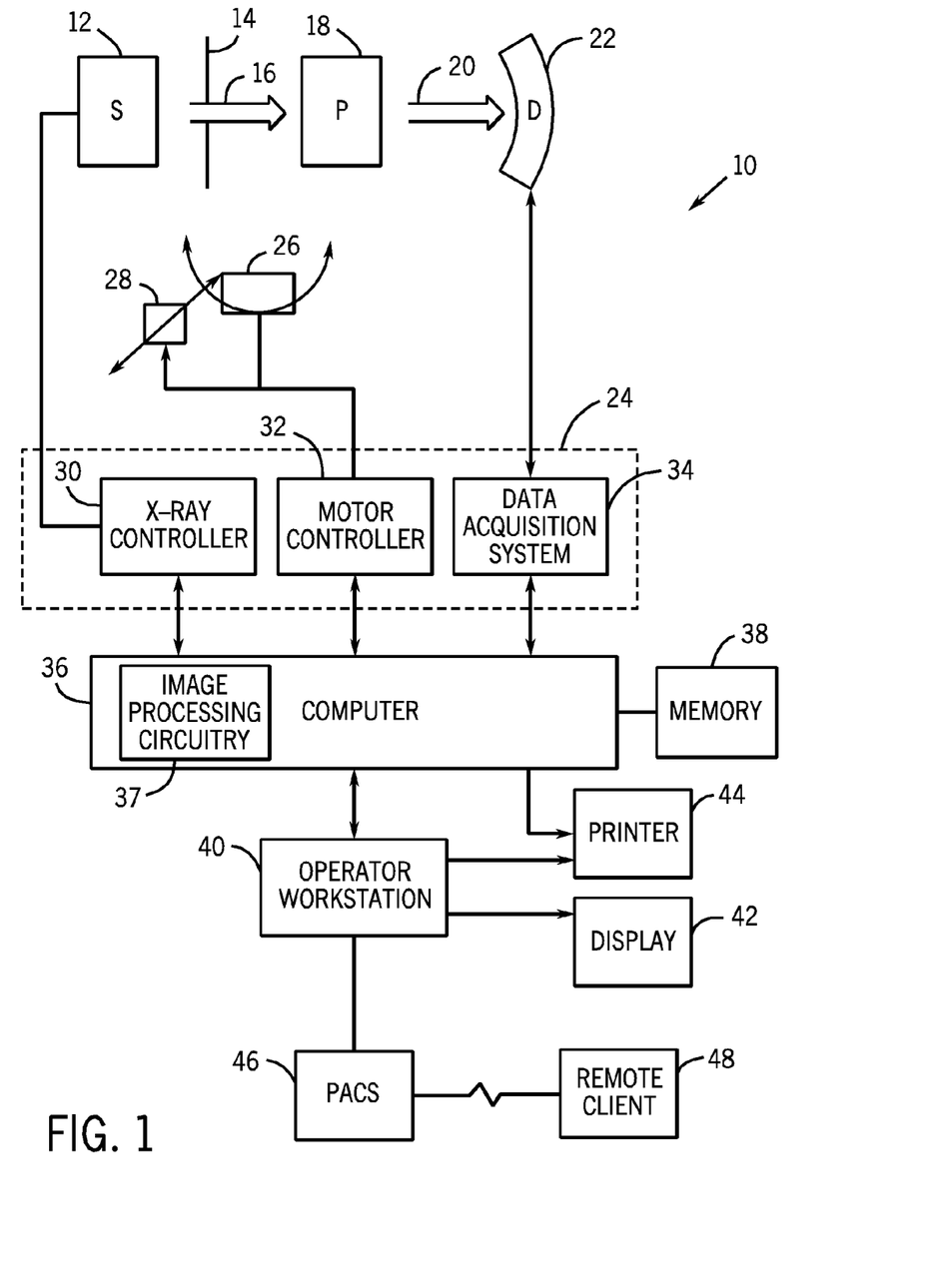
FIG. 1 is a diagrammatical illustration of an exemplary CT imaging system, in accordance with an embodiment of the present disclosure.

Turning now to the figures, FIG. 1 is a diagram that illustrates an imaging system 10 for acquiring and processing image data. In the illustrated embodiment, system 10 is a CT system designed to acquire X-ray projection data, to reconstruct the projection data into a tomographic image, and to process the image data for display and analysis, in accordance with the present technique. Though the imaging system 10 is discussed in the context of medical imaging, the techniques and configurations discussed herein are applicable in other non-invasive imaging contexts, such as security screening or industrial nondestructive evaluation of manufactured parts. In the embodiment illustrated in FIG. 1, the CT imaging system 10 includes an X-ray source 12. As discussed in detail herein, the source 12 may include one or more conventional X-ray sources, such as an X-ray tube, or a distributed source configured to emit X-rays from different locations along a surface. For example, the source 12 may include one or more addressable solid-state emitters. Such solid-state emitters may be configured as arrays of field emitters, including one-dimensional arrays, i.e., lines, and two-dimensional arrays.

The source 12 may be positioned proximate to a collimator 14. The collimator 14 may consist of one or more collimating regions, such as lead or tungsten shutters, for each emission point of the source 12. The collimator 14 typically defines the size and shape of the one or more X-ray beams 16 that pass into a region in which a subject 18, such as a human patient, is positioned. Each X-ray beam 16 may be generally fan-shaped or cone-shaped, depending on the configuration of the detector array and/or the desired method of data acquisition, as discussed below. An attenuated portion 20 of each X-ray beam 16 passes through the subject 18 and impacts a detector array, represented generally at reference numeral 22.

The detector 22 is generally formed by a plurality of detector elements that detect the X-ray beams 16 after they pass through or around the subject 18. Each detector element produces an electrical signal that represents the intensity of the X-ray beam 16 incident at the position of the detector element when the beam strikes the detector 22. Alternatively, each element of detector 22 may count incident photons in the X-ray beam 16 and may also determine their energy. Typically, the X-ray beam 16 is generated and the corresponding electrical signals are acquired at a variety of angular positions around the subject of interest so that a plurality of radiographic projection views can be collected. The electrical signals are acquired and processed to reconstruct an image that is indicative of the features within the subject 18, as discussed in further detail below.

A system controller 24 commands operation of the imaging system 10 to execute examination protocols and to process the acquired data. The source 12 is typically controlled by a system controller 24. Generally, the system controller 24 furnishes power, focal spot location, control signals and so forth, for the CT examination sequences. The detector 22 is coupled to the system controller 24, which commands acquisition of the signals generated by the detector 22. The system controller 24 may also execute various signal processing and filtration functions, such as initial adjustment of dynamic ranges, interleaving of digital image data, and so forth. In the present context, system controller 24 may also include signal-processing circuitry and associated memory circuitry. As discussed in greater detail below, the associated memory circuitry may store programs and/or routines (such as programs and/or routines suitable for correcting or reducing artifacts in an iterative reconstruction implementation, as disclosed herein) executed by the system controller 24 or a processor-based system in communication with the system controller 24. Further, the memory circuitry of the system controller 24 may also store configuration parameters, image data, and so forth. In one embodiment, the system controller 24 may be implemented as all or part of a processor-based system such as a general purpose or application-specific computer system.

In the illustrated embodiment of FIG. 1, the system controller 24 may control the movement of a linear positioning subsystem 28 and a rotational subsystem 26 via a motor controller 32. In an embodiment where the imaging system 10 includes rotation of the source 12 and/or the detector 22, the rotational subsystem 26 may rotate the source 12, the collimator 14, and/or the detector 22 about the subject 18. It should be noted that the rotational subsystem 26 might include a gantry comprising both stationary components (stator) and rotating components (rotor). The linear positioning subsystem 28 may enable the subject 18, or more specifically a patient table that supports the subject 18, to be displaced linearly. Thus, the patient table may be linearly moved within the gantry or within an imaging volume (e.g., the volume located between the source 12 and the detector 22) and enable the acquisition of data from particular areas of the subject 18 and, thus the generation of images associated with those particular areas. Additionally, the linear positioning subsystem 28 may displace the one or more components of the collimator 14, so as to adjust the shape and/or direction of the X-ray beam 16. In embodiments comprising a stationary source 12 and a stationary detector 22, a mechanical rotational subsystem may be absent, with emitters spaced at different angular locations about the subject instead being activated at different times to allow acquisition of projections at different angles. Similarly, in embodiments in which the source 12 and the detector 22 are configured to provide extended or sufficient coverage along the z-axis (i.e., the axis associated with the main length of the subject 18) and/or linear motion of the subject is not required, the linear positioning subsystem 28 may be absent.

The source 12 may be controlled by an X-ray controller 30 disposed within the system controller 24. The X-ray controller 30 may be configured to provide power and timing signals to the source 12. In addition, in some embodiments the X-ray controller 30 may be configured to selectively activate the source 12 such that tubes or emitters at different locations within the system 10 may be operated in synchrony with one another or independent of one another.

Further, the system controller 24 may comprise a data acquisition system 34. In such an embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a processor-based system, such as a computer 36. Alternatively, in other embodiments, the detector 22 may convert the sampled analog signals to digital signals prior to transmission to the data acquisition system 34.

In the depicted embodiment, a computer 36 is coupled to the system controller 24. The data collected by the data acquisition system 34 may be transmitted to the computer 36 for subsequent processing and reconstruction. For example, the data collected from the detector 22 may undergo pre-processing and calibration at the data acquisition system 34 and/or the computer 36 to produce representations of the line integrals of the attenuation coefficients of the subject 18 and the scanned objects. In one embodiment, the computer 36 contains image-processing circuitry 37 for processing and filtering the data collected from the detector 22. The processed data, commonly called projections, may then be reconstructed by the image processing circuitry 37 to form an image of the subject 18 and/or the scanned area. In one implementation, the projections are reconstructed into an image by using one or more reconstruction algorithms, such as in accordance with an iterative reconstruction technique as discussed herein. Once reconstructed, the image produced by the system 10 of FIG. 1 may reveal an internal region of interest of the subject 18 which can be used for diagnosis, evaluation, and so forth.

The computer 36 may comprise or communicate with a memory 38 that can store data processed by the computer 36, data to be processed by the computer 36, or routines and/or algorithms to be executed by the computer 36, such as for processing image data in accordance with the present technique. It should be understood that any type of computer accessible memory device capable of storing the desired amount of data and/or code may be utilized by such a system 10. Moreover, the memory 38 may comprise one or more memory devices, such as magnetic, solid-state, or optical devices, of similar or different types, which may be local and/or remote to the system 10. The memory 38 may store data, processing parameters, and/or computer programs comprising one or more routines or algorithms for performing the iterative reconstruction and/or the artifact correction processes described herein.

The computer 36 may also be adapted to control features enabled by the system controller 24 (i.e., scanning operations and data acquisition). Furthermore, the computer 36 may be configured to receive commands and scanning parameters from an operator via an operator workstation 40 which may be equipped with a keyboard and/or other input devices. An operator may, thereby, control the system 10 via the operator workstation 40. Thus, the operator may observe from the computer 36 the reconstructed image and other data relevant to the system 10, initiate imaging, select and apply image filters, and so forth. Further, the operator may manually identify and/or review features and regions of interest from the reconstructed image. Automated detection algorithms may be applied to aid in identifying and/or manipulating the features or regions of interest.

As illustrated, the system 10 may also include a display 42 coupled to the operator workstation 40. The display 42 may be utilized to observe the reconstructed images, for instance. Additionally, the system 10 may include a printer 44 coupled to the operator workstation 40 and configured to print a copy of the one or more reconstructed images. The display 42 and the printer 44 may also be connected to the computer 36 directly or via the operator workstation 40. Further, the operator workstation 40 may include or be coupled to a picture archiving and communications system (PACS) 46. It should be noted that PACS 46 might be coupled to a remote system 48, radiology department information system (RIS), hospital information system (HIS) or to an internal or external network, so that others at different locations can gain access to the image data.

Although only one operator workstation is depicted, one or more operator workstations 40 may be linked in the system 10 for outputting system parameters, requesting examinations, viewing images, and so forth. In general, displays 42, printers 44, workstations 40, and similar devices supplied within the system 10 may be local to the data acquisition components, or may be remote from these components, such as elsewhere within an institution or hospital, or in an entirely different location, linked to the image acquisition system 10 via one or more configurable networks, such as the Internet, virtual private networks, and so forth.

Although the previous discussion discloses typical embodiments of the imaging system 10, other system configurations may be employed to acquire image data. The image reconstruction process performed on an imaging system 10 is often based on filtered backprojection techniques. The filtered backprojection technique generally involves the steps of weighting, filtering, and backprojecting the acquired sinogram data. As may be appreciated, the sinogram is a representation of the data collected by the data acquisition system 34 of FIG. 1. In particular, for single-row detectors, the sinogram is a two-dimensional dataset, $p(s,\theta)$, obtained by stacking the one-dimensional projections, $p_\theta(s)$, where $\theta$ is the view angle of data acquisition, and s is the detector element. For multi-row detectors, the sinogram becomes a three-dimensional dataset. Some of the techniques described herein may be discussed in the context of a two dimensional sinogram for simplicity, but the application to three dimensions is straightforward, if not identical. Thus, the sinogram is a collection of output data from the detector array 22 resulting from radiation traversing the subject of interest 18 at a given source position. The output data from each source and detector position or view corresponds to a row of projection data in the sinogram. Thus, each row of the sinogram constitutes a projection view that is indicative of the attenuation information for a distinct view angle, for given source and detector positions, with respect to the subject 18.

Except for objects lying at the center of the CT system 10, all attenuating objects (e.g., tissue, bone, contrast agent, and so forth) within the field of view will appear in the sinogram as a sine-like wave, whose position corresponds to their location in the subject of interest. That is, the location of particular data resulting from attenuation by an object or region may appear as a distinguishable sinusoidal trace. Thus, for a static point in the imaging area and a parallel beam X-ray source, the sinogram does indeed possess a sinusoidal form. However, in the presence of motion within the imaging area, the sinogram or portions of the sinogram will deviate from the sinusoidal form.

In accordance with a filtered backprojection reconstruction, the weighting of the sinogram data may involve point-by-point multiplication by a pre-calculated 2D array (for single-row detector systems) or 3D array (for multi-row detector systems). The filtering or convolution step filters the sinogram data to decorrelate them and may be carried out as a series of one-dimensional convolutions. In the backprojection step, the measured sinogram data is added to all picture elements in an image along the projection lines of the original projection views.

While such filtered backprojection reconstructions are computationally fast to perform, other reconstruction techniques may also be performed and may be favored for various reasons, such as image quality, noise reduction, increased spatial resolution, suitability with incomplete data, low-dose suitability, and so forth. For example, iterative reconstruction techniques (such as model-based iterative reconstruction (MBIR)) may be employed to reconstruct the projection data into useful images. Iterative image reconstruction techniques utilize a variety of algorithms that incorporate various assumptions or expectations with respect to the acquired image data. For example, an idealized or expected image for the anatomy of interest may be modeled (taking into account system geometry and settings, scan protocol, and so forth) to generate a reconstruction model that is used in the reconstruction process. Likewise, a system model (i.e., a geometric and physical representation of the imaging system during image data acquisition) may be employed to relate the image space to the projection space via a number of computed coefficients for each voxel/view pair. Projections based on the reconstruction model may be computed (using the system model) and compared to the actual acquired image data using statistical modeling techniques. The differences between the acquired image data and the reconstruction model may be used to update or incrementally modify the generated (i.e., back-projected) image. This process may be repeated for a set number of iterations, until the differences are below some threshold value (i.e., convergence), or until the criteria of a governing cost function are satisfied.

Iterative image reconstruction may be susceptible to inconsistencies in the projection data relative to the reconstruction model, which may manifest as artifacts in the reconstructed images. In particular, the iterative reconstruction algorithm may try to converge on the image that best explains the inconsistent measurements, which may result in images containing artifacts. For example, CT images generated using iterative reconstruction techniques may be susceptible to artifacts related to motion during acquisition of the image data, especially to the extent that the reconstruction model does not explicitly account for such motion. Likewise, noise or poor calibration of the imaging system may lead to inconsistencies in the acquired image data that may result in image artifacts. Further, if the data is acquired using a helical scan protocol (i.e., linear displacement of the subject during rotation of the source and detector), the geometric characteristics of the helical acquisition can result in data inconsistencies that generate image artifacts.

In certain instances, an iterative reconstruction algorithm may enhance such artifacts when data inconsistencies are present. In particular, artifacts may be more pronounced in regions of stronger gradient of the backprojection weight. That is, artifacts may be enhanced in circumstances where the image volume receives non-uniform contributions from the system model during the backprojection process, due to some voxels receiving contributions from more views than other voxels. Thus, the resulting artifacts may be stronger where the backprojection contribution varies more strongly from voxel to voxel.

Problems such as these that are associated with non-uniform contributions in the backprojection may be present primarily in helical scan acquisitions and iterative reconstruction implementations. For example, the quality of images generated using iterative reconstruction may be degraded by rotational artifacts observed from slice to slice. These artifacts may manifest as shading and/or banding streaks in axial and reformat images. Likewise, artifacts attributable to patient or object motion during data acquisition may result in streaks and shading in images generated using iterative reconstruction techniques if the motion is not explicitly accounted for in the modeling process.

With the foregoing discussion in mind, the following approaches may be used, alone or in conjunction with one another or other techniques, to address artifacts generated using iterative reconstruction algorithms. For example, in one implementation, a voxel-dependent angular weighting function may be employed to modulate non-uniformities in the number of views contributing to each voxel. In particular, in calculating the update for a current voxel, iterative reconstruction techniques will typically utilize all available image data. As noted above, such an approach may be subject to artifacts due to the large differences in the amount of data (e.g., views) contributing to each voxel.

Figure 2:
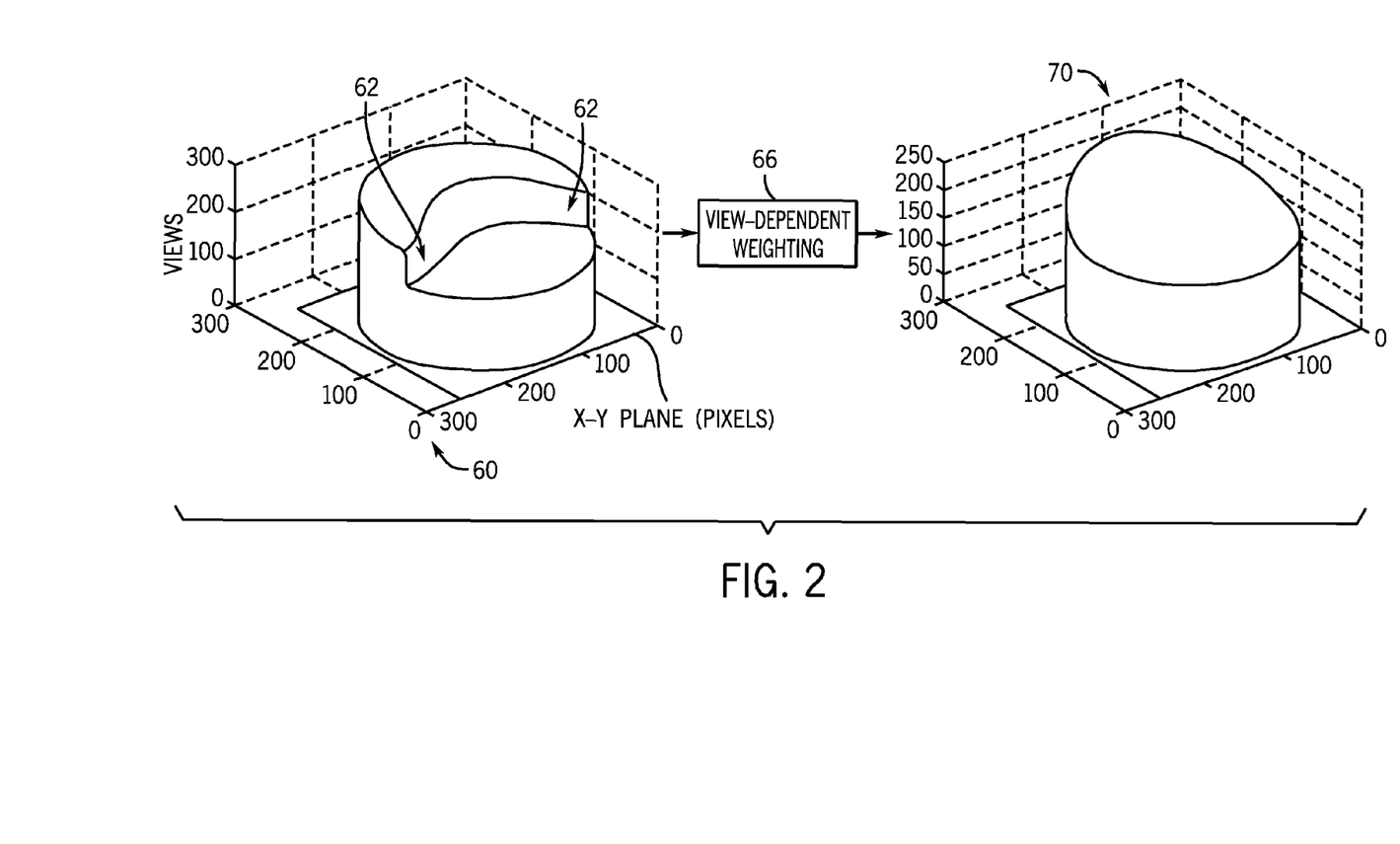
FIG. 2 depicts a view-dependent weighting performed on a set of helical scan data to generate more uniform view contributions for each voxel, in accordance with one embodiment of the present disclosure.

To reduce or eliminate these artifacts, a specific angular weighting (e.g., a view dependent weighting) may be applied to the data contributing to each voxel so that the amount of data used for each voxel becomes more uniform, thereby reducing artifacts. In certain implementations, the weighting function may be a trapezoidal-shaped weighting function or a rectangular-shaped weighting function (which is equivalent to modifying the angular range). For example, referring to FIG. 2, an initial set 60 of helical scan data (acquired at a pitch of 1.0) illustrates the number of views contributing to each voxel. As depicted by the sharp drop-offs 62, there may be abrupt and sharp transitions in the data set 60 where the number of views contributing to proximate voxels changes. Such abrupt changes or drop-offs may be associated with artifacts in the reconstructed images. As depicted in FIG. 2, a view-dependent weighting function 66 may be defined for the initial scan data 60. In the depicted example, the view dependent weighting function 66 increases the uniformity of the amount of data used for each voxel. This increased uniformity of the amount of data used for each voxel (as depicted in weighted data set 70) may result in fewer and/or less severe artifacts in the images generated using iterative reconstruction techniques.

By way of example, for plane z=0 and considering all point x,y in that plane, in a helical scan there can be one or more continuous segments of views that contribute to a given voxel. Typically there may be a single continuous segment, but there may be more than one continuous segment depending on the pitch associated with the data acquisition. The total number of views available for voxel (x,y), i.e., Tol_Ang (x,y) is equal to:

$$\text{Tol\_Ang}(x, y) = \sum_i (\text{Ang\_e}_i(x, y) - \text{Ang\_b}_i(x, y)) = \text{length}(\text{Ang\_vec}(x, y)) \quad (1)$$

where [Ang_b$_i$(x, y), Ang_e$_i$(x, y)) is the ith continuous view segment and where $$\text{Ang\_vec}(x, y) = \bigcup_i [\text{Ang\_b}_i(x, y), \text{Ang\_e}_i(x, y)).$$

As noted above, Tol_Ang(x, y) may not be a smooth function of (x,y), as demonstrated by data set 60 of FIG. 2. To smooth the variation in the amount of data contributing to each voxel in plane (x,y) (i.e., to remove or reduce the sharp drop-offs 62 of FIG. 2) a smoothing function may be applied (i.e., diffusion, low pass filtering, and so forth) to generate $\tilde{T}ol\_Ang(x, y)$.

An angular weighting function can then be defined such that the contribution to voxel (x,y) is scaled by Wght(x, y) so that:

$$\tilde{T}ol\_Ang(x,y) = Ang\_vec(x,y) \cdot Wght(x,y)' \quad (2)$$

The angular range modulation function defined by Equation (2) will be used as a weighting on the projection data before or during backprojection in the iterative reconstruction process. In one embodiment, the weight provided by the angular modulation function is only involved in calculating the update for the backprojection step.

A similar approach may also be useful in reducing motion artifacts. In one such implementation, instead of smoothing the amount of data (angular range) for each voxel, as described above, a smaller angular range, i.e., less data, may be used to improve the temporal resolution of the iterative reconstruction. In one embodiment, this may be accomplished by applying an angle-dependent weighting. For example, a maximum weight of 1.0 may be applied at the center view for a voxel and this weight may be tapered down to 0.0 for the views furthest away from the center view.

In one embodiment, to minimize the loss of data and preserve the noise benefits of iterative reconstruction, the narrowing of the angular range may be applied to voxels identified as being subject to motion. For example, to identify voxels where motion appears to be occurring, the residual error sinogram of the iterative reconstruction may be analyzed. As will be appreciated, larger errors may be observed in the residual error sinogram to the extent such motion is not explicitly accounted for by the model. Regions of motion thus identified may then be subjected to a narrowing of the angular range for the relevant voxels as discussed above to effectively increase the temporal resolution for those voxels subject to motion. Alternatively, in another embodiment, separate reconstructions can be performed for those regions of the image subject to motion and for those regions not subject to motion, with the separate reconstructions having different shifts in the centers of the angular ranges. For the regions of the image subject to motion, the density of those voxels will vary based on the respective reconstruction.

One consequence of the use of a view dependent weighting scheme, as discussed herein, may be that different voxels are updated using different cost functions. However, it is also possible that the view-dependent weighting function can be tuned for each voxel to eliminate or reduce the computational impact of using multiple cost functions for image convergence or to otherwise improve image quality on a voxel-by-voxel basis.

In addition to such view or angle-dependent weighting schemes, other artifact reduction implementations are presently contemplated. For example, in one embodiment, a projection domain weighting may be applied (which may be voxel independent and/or view independent). Unlike the previously described view or angle-dependent weighting schemes, such projection domain weighting approaches do not modulate the amount of data on a voxel by voxel basis. Instead, a smoothed detector-weighting window can be applied to all the projections in addition to the original statistical weighting applied in iterative reconstruction. The effect of this detector-weighting function is to provide a lower weight to some or all of the projection data corresponding to specific regions on the detector. Thus, in such an approach, instead of discarding data on a view or angle basis, data within the projection domain may instead be sacrificed to reduce or eliminate data inconsistencies that may lead to reconstruction artifacts. In general, any weighting function can be used. In other words, the statistical weights used typically in the iterative reconstruction algorithm will be augmented with detector-channel dependent weights, which depend on the geometrical aspects of the scanner and the scan protocol, to enhance uniformity in the backprojection.

Figure 3:
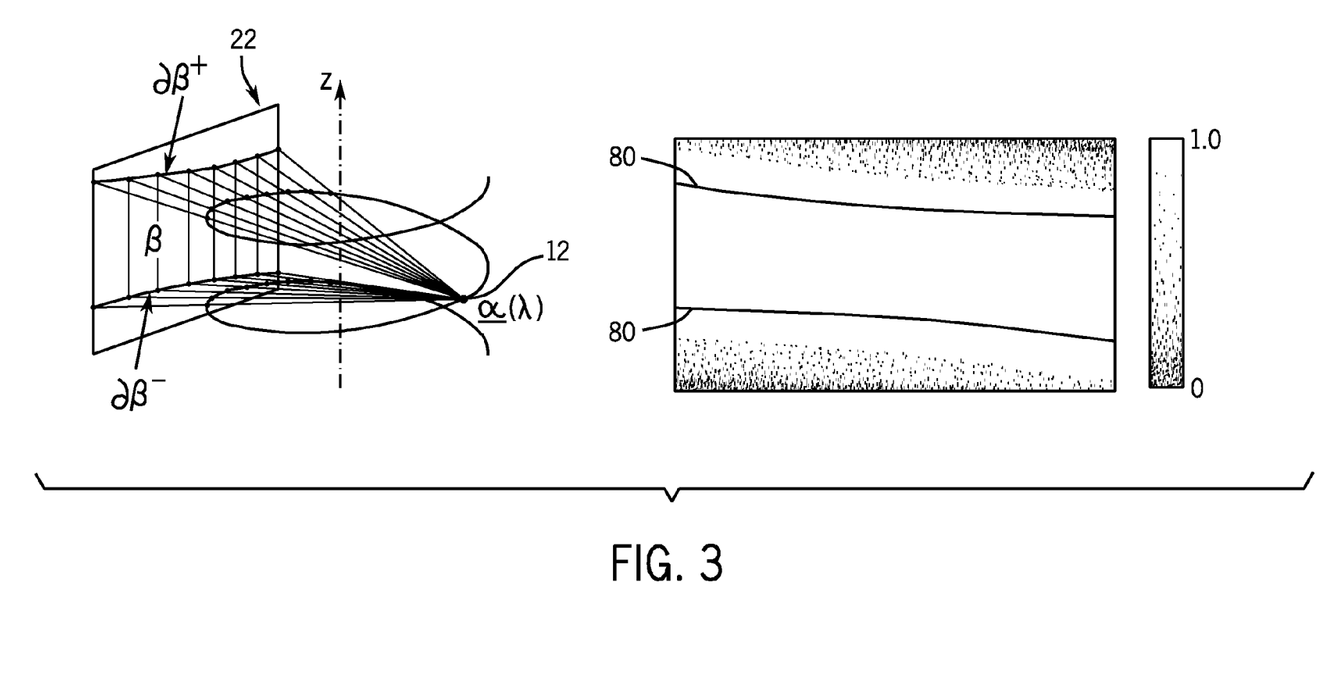
FIG. 3 depicts a geometrical description of a Tam window associated with a helical scan, in accordance with one embodiment of the present disclosure.

For example, in one embodiment the Tam window is used as the detector weighting function. The Tam window is the minimum data needed to reconstruct a voxel in a helical scan and is known in analytic (i.e., non-iterative) reconstruction theory. In particular, the Tam window is the region bounded, in the detector, by the cone-beam projection of the upper and lower turns of the helix. An example of a Tam window and its geometrical definition are provided in FIG. 3. As depicted, the upper and lower boundaries 80 may be obtained by looking from the source 12 and projecting the helical trajectory onto the detector 22. In an embodiment in which the Tam window is used as the detector weighting function, the total backprojection contribution to different voxels (i.e., the total number of views contributing to each voxel) changes very smoothly. One side effect of using the Tam window as the weighting function in iterative reconstruction is that data in the corners of the detector 22 may be unused, which may affect dose efficiency and noise level in the images.

With respect to artifact reduction as discussed herein, the goal is to achieve a smoothly varying contribution in the backprojection while maintaining relatively low noise levels. In one embodiment, the Tam window may be artificially enlarged and the edges of the Tam window feathered to generate a larger and smoother window function in the detector domain. Such modifications of the Tam window may yield a suitable tradeoff between increased noise and lower artifacts. Other, ad hoc detector window functions may also be applied (such as rectangular or trapezoidal window functions) with or without feathering.

Figure 4:
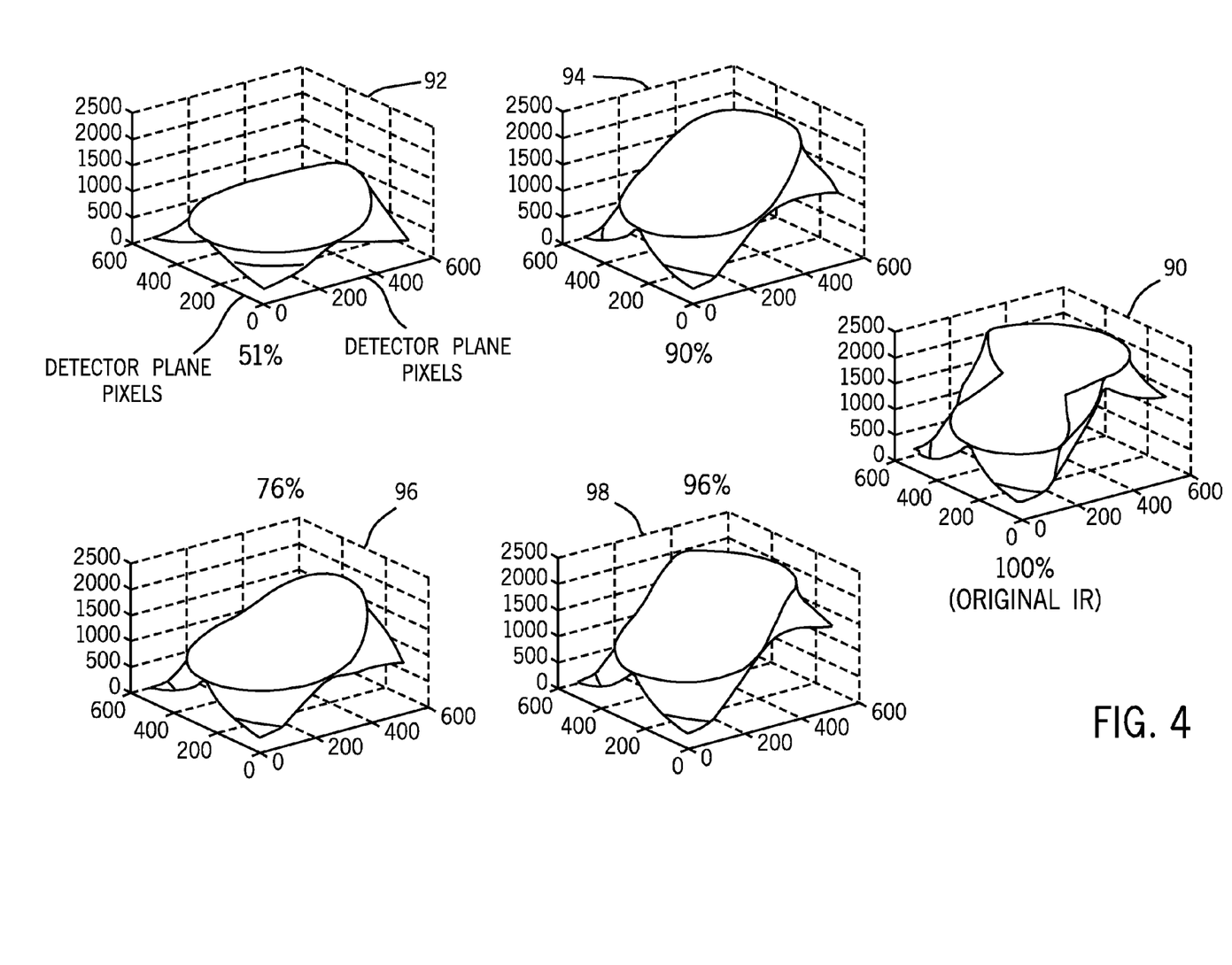
FIG. 4 depicts the amount of projection data available using different window functions based on the Tam window, in accordance with one embodiment of the present disclosure.

For example, turning to FIG. 4, the amount of data from different window functions based on the Tam window is depicted. In particular, the different graphs of FIG. 4 depict the change and the uniformity of the system model data for the different window functions. In FIG. 4, a depiction of the projection data used in a conventional iterative reconstruction, which uses 100% of the projection data, is depicted by graph 90. As evidenced by the surface of the depicted projection data of graph 90, the projection data used is not uniform, leading to steep gradients and surface irregularities. Likewise, graph 92 depicts projection data used when an unmodified Tam window is applied as a detector weighting function, i.e., when the minimum data (approximately 50% of the projection data) needed to reconstruct a voxel in a helical scan (pitch=1.0) is used. As evidenced by the surface of the depicted projection data of graph 90, the projection data used is generally uniform, with only a weak gradient and few or no surface irregularities. Graphs 94, 96, 98 depict the percent of projection data used, and its corresponding uniformity, when modified Tam windows (i.e., enlarged Tam windows and/or Tam windows with feathered edges) are applied as a detector weighting function. As depicted, the modified Tam windows may allow the use of more projection data while still reducing the gradient and improving the uniformity of the projection data relative to the conventional iterative reconstruction (depicted by graph 90). As depicted by graphs 92, 94, 96, 98, by using a weighted window function and less than 100% of the projection data, the data surface may be smoothed such that irregularities and steep gradients in the conventional reconstruction data (depicted by graph 90) may be removed or reduced, thereby reducing potential data inconsistencies and artifacts in the reconstructed images.

For example, for a cylindrical detector the upper and lower boundaries of the Tam window are defined as:

$$B^+(\alpha), B^-(\alpha) \qquad (3)$$

respectively, where α is the fan angle in the x-y plane. In accordance with this window function, values within the window are weighted by a value of 1 (i.e., given their full value); values outside the window are weighted by a value of 0 (i.e., given no weight). An extended or enlarged Tam window may be defined as:

$$B^+(\alpha)+k, B^-(\alpha)-k \qquad (4)$$

where k is a small shift to make a larger window to allow the use of more data in the iterative reconstruction process. As noted above, some feathering may also be applied at the shifted Tam window boundaries to make a smooth transition. Thus, due to the feathering, values within the window are weighted by a value of 1 (i.e., given their full value); values outside the window are weighted by a value of 0 (i.e., given no weight), and values at the boundary of the window are given a weight between 0 and 1 such that a smooth transition occurs at the edge of the window between full weighting and no weighting. In one embodiment, these weights (i.e., 0, 1, and between 0 and 1 at the window boundary) are multiplied with the original iterative reconstruction statistical weights prior to backprojection.

In certain implementations, artificial data outside the real detector boundary may be synthesized to make the detector artificially larger. In such an implementation, the weighting function (e.g., window) may be made even larger and may allow the use of more real data. The boundary of the window function may be pushed out further (i.e., larger k) such that a larger fraction of the actual measured data receives a non-zero weight. The synthetic data may be generated using extrapolation and/or through reprojection of intermediate images. Such an approach may eliminate the noise penalty of other approaches but may slightly increase reconstruction time due to the generation of and use of the synthesized data points used in the reconstruction.

The projection-based approaches discussed herein may also provide benefits with respect to motion artifact reduction in two ways. First, the smooth transition of the window may lessen streaks attributable to motion. Second, a smaller temporal window (i.e., higher temporal resolution) may be utilized to keep the consistency in the moving sinogram as high as possible. For example, the moving portion of the sinogram may be weighted downward (i.e., given less weight), giving less emphasis to that portion of the data when calculating updates for the next steps or iterations. Thus, the artifacts caused by the inconsistencies in the sinogram that are attributable to motion may be reduced.

Figure 5:
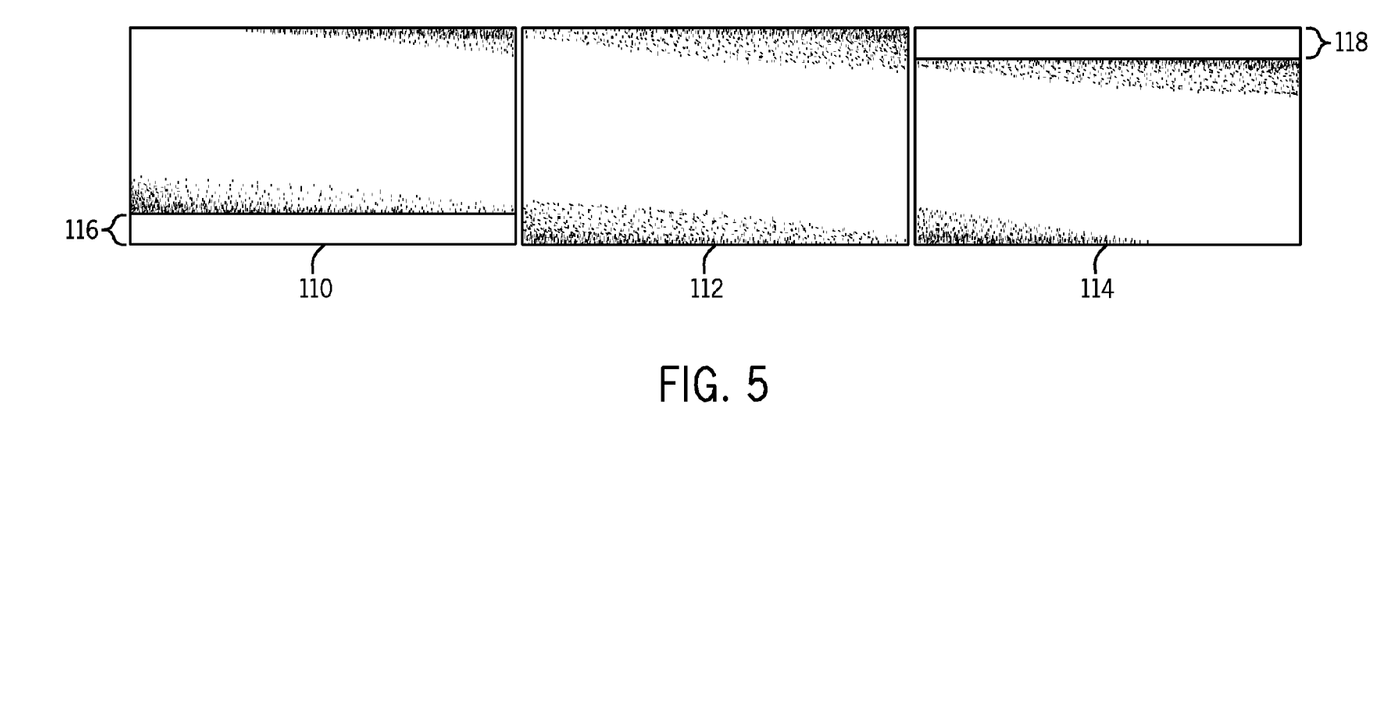
FIG. 5 depicts three variant Tam windows that are offset from one another along the row direction, in accordance with one embodiment of the present disclosure.

While the preceding approaches reduce data utilization, and may thereby increase noise in the reconstructed images, other approaches may avoid these issues. For example in one embodiment, multiple shifted versions of overlapping or proximate images may be reconstructed, using the one or both of the preceding approaches, and combined to form a diagnostic image. In a view or angular weighting implementation, the view weighting intervals are shifted in the view (i.e., time) direction to generate temporally offset images. In a projection-weighted implementation, the projection weighting can be shifted in the detector row (i.e., time) direction to generate temporally offset images. For example, referring to FIG. 5, three different Tam windows 110, 112, 114 are depicted which are offset (offsets 116 and 118) from one another in the row (time) direction. In one embodiment, the three temporally offset Tam windows 110, 112, 114 cover a full 360° or more in the aggregate, though the individual windows each cover less than the full 360°. The shifted images, such as the offset images depicted in FIG. 5, can be averaged or combined in generating the final diagnostic image.

Such an approach results in a reconstruction using a smaller temporal window, which may be suitable for a reconstruction where motion is present. As noted above, each temporally offset window has less than a full 360° of data, such as 180° of data, but the temporally offset windows maybe combined to provide the full 360° or more of data. The data associated with each temporally offset window may be separately reconstructed, with each reconstruction being uncorrelated, i.e., independent, of the others. In one embodiment, the same or different Fourier masks may be utilized in generating each separate image. The final image may then be generated as an average of the separate reconstructions.

This approach provides two potential advantages. First, noise may be reduced by combining the information (or statistics) from the multiple temporally offset reconstructions. Second, artifacts may be reduced by averaging or combining multiple images with different artifact content.

Further, this approach is suitable for use in model-based iterative reconstruction where large data inconsistencies are present, such as due to motion by or in the subject being imaged. Instead of utilizing pure 4D object reconstruction (such as utilizing motion vector estimation and/or motion compensation) a rough dynamic iterative reconstruction may be used to approximate the motion effect on each voxel, i.e., the voxel value can change dynamically instead of being held to a constant value. For example, two or more separate reconstructions may be performed on different temporal windows to reconstruct an image in two or more points in time (i.e., phases). A voxel representing a region where no motion is present will have the same value in the separate reconstructions, while a voxel representing a region where motion is present will not have the same value in the separate reconstructions, i.e., the voxel will change density in the different reconstructions. Further, the artifacts pattern will differ in the separate reconstructions. Therefore, in one embodiment, combining the separate reconstruction images may result in the same noise level (the non-motion region) and reduced artifacts (motion region).

The separate, offset reconstructed images can be combined by a variety of techniques. For example, in one implementation, the separate reconstructions may be combined by averaging or adding the reconstructed images. In another implementation, the separate reconstructions may be combined by computing a weighted combination based on the artifact level (i.e., the variance level). For example, greater weight may be given to those reconstructed images with less artifacts, i.e., less variance. In a further implementation, the separate reconstructions may be combined by Fourier domain blending. As may be appreciated, streaks in the different reconstructed images may correspond to different Fourier orientations and different Fourier masks may be used in the generation of each reconstructed image. In yet another implementation, the separate reconstruction may be combined by estimating and compensating relative object motion in the reconstructions prior to averaging.

While the preceding discussion described the separate and uncorrelated, i.e., independent, reconstruction of each offset window of data, in other embodiments the reconstruction processes may be correlated. In particular, it may be computationally efficient to jointly reconstruct the two or more sets of data with one objective function, such as temporally offset image or projection data. For example, to the extent that a portion of the forward projection calculation may use the same geometry for different offset windows, this calculation can be shared in a joint reconstruction.

In addition, joint reconstruction may provide image quality benefits, such as by regularizing the differences between the two states or, for example, using a norm that encourages sparseness, such as the L1-norm. In particular, during the iteration process, information from other reconstructions may be used to update or weight regions of greater consistency. For example, each reconstruction process may be related to try to minimize differences between the images reconstructed from the different windows of data, i.e., to get a good correlation between the reconstructed images. In one embodiment, the differences between the two reconstructions may be minimized, as the static regions should already be similar or identical. For example, by doing a joint estimation of the multiple states, i.e., data windows, the voxels corresponding to regions of motion may be identified due to their having more than one state.

In a further implementation, different weighting may be utilized on different reconstruction regions. For example, more homogeneous regions in the respective windows or sets of image data, i.e., regions having fewer differences, may be more heavily weighted. Correspondingly, less homogeneous regions in the respective windows or sets of image data (i.e., regions having greater differences) may be more lightly weighted or may even be given a zero weight. Once the respective reconstructions are generated for each respective window of image data, the reconstructions may be combined, such as using one or more of the techniques described above.

In another embodiment, the backprojection can be modified further to make the contribution to each voxel more uniform across x, y, z. One such approach is to apply fan-to-parallel rebinning to the data. In particular, parallel beam (or cone-parallel) datasets do not have an 1/r dependence in the backprojector, where r represents the source-to-voxel distance. Thus, in such an approach, conjugate views will have a more similar contribution, making the backprojection, and thus the update step, more uniform.

Alternatively, the backprojection weights may be explicitly modified to remove the 1/r dependence. In such an implementation, the backprojector geometrically stays in the original cone-beam geometry, but this is compensated by modifying the backprojection weights by a factor:

$$r(x,y)/r\_0 \quad (5)$$

such that the new backprojection weight in a given view is:

$$1/r(x,y)*r(x,y)/r\_0=1/r\_0 \quad (6)$$

which is independent of (x,y). Thus, in such embodiments, the 1/r dependence may be compensated, thereby reducing or eliminating the effects of the scanning geometry.

Figure 6:
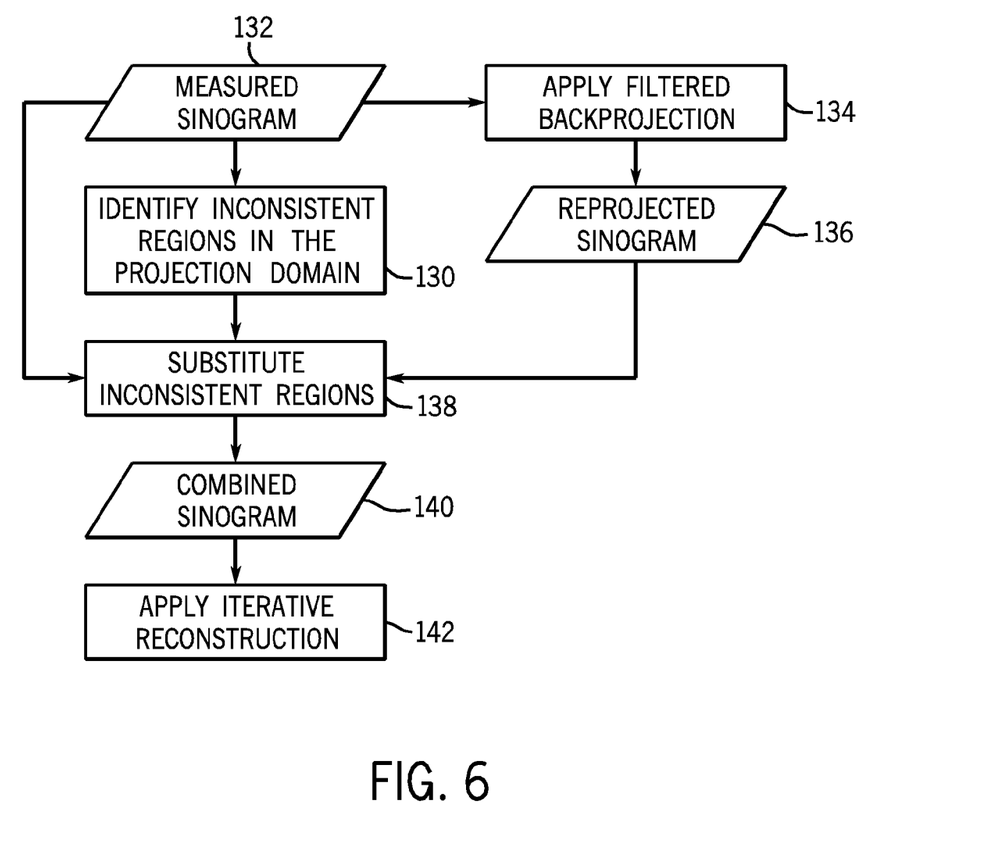
FIG. 6 depicts a flowchart of steps for generating a blended sinogram of corrected projection data, in accordance with one embodiment of the present disclosure.

In another embodiment, the projection may be corrected to improve consistency and to thereby improve the results of an iterative reconstruction process. Turning now to FIG. 6, in one such embodiment, the inconsistent projection data is identified (block 130), such as by identifying portions of the error sinogram (i.e., measured sinogram 132) containing significant error, which likely corresponds to inconsistency in the projection data. The inconsistent projection data thus identified may be substituted (block 138) with synthesized data (i.e., reprojected sinogram 136) from a filtered backprojection (FBP) reconstruction 134 (which typically generates fewer motion artifacts than iterative reconstruction) performed on the same scan data (i.e., measured sinogram 132). The substitution of the inconsistent projection data with the synthesized projection data results in a set of blended data (i.e., combined sinogram 140) that may be iteratively reconstructed (block 142) to generate reconstructions with fewer artifacts. That is, for regions of the projection data containing motion artifacts, synthesized projection data is substituted to allow images to be iteratively reconstructed with fewer motion artifacts.

In further embodiments, the cost function employed in the iterative reconstruction may be modified so as to reduce motion-based artifacts in the reconstructed images. For example, in one embodiment, the cost function may be modified to discount significant large errors in the error sinogram attributable to inconsistencies in the projection data. The cost function typically increases or decreases in proportion to the presence of a large residual error in the sinogram, e.g., the larger the residual error in the sinogram, the greater the increase in the cost function. In one implementation, a threshold may be established beyond which the cost function does not increase or decrease when the residual error crosses the threshold. That is, the cost function may increase as the residual error increase up to the point when the residual error exceeds the established threshold. Once the residual error exceeds the threshold, however, the cost function no longer increases. In accordance with this approach, the effects of large errors, such as errors associated with motion, may be reduced or eliminated by limiting the adjustment made to the cost function by use of a threshold.

Technical effects of the invention include the generation of images using iterative reconstruction techniques. Technical effects also include the generation of iteratively reconstructed images with reduced or corrected motion artifacts. Technical effects also include the generation of iteratively reconstructed images corrected for the effects of a helical data acquisition. In certain embodiments, these technical effects may be achieved by using something less than all available scan or projection data for each voxel.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An image reconstruction method, comprising the acts of:
   accessing scan data acquired using a computed tomography system, wherein the scan data comprises temporally offset scan data;
   computing a voxel-dependent angular weighting function corresponding to the scan data;
   using the respective weighting function to iteratively compute a set of images from the scan data, such that the angular range of the data contributing to each voxel is made more uniform and/or the angular range is narrowed for one or more voxels;
   independently reconstructing images generated based on the temporally offset scan data to generate one or more temporally offset images; and
   combining the temporally offset images using one or more of averaging, addition, weighted combination, or Fourier combination.

2. The image reconstruction method of claim 1, wherein the angular weighting function is view dependent.

3. The image reconstruction method of claim 1, wherein the angular weighting function is one of a trapezoidal weighting function or a rectangular weighting function.

4. The image reconstruction method of claim 1, wherein the scan data comprises helical scan data.

5. The image reconstruction method of claim 1, wherein the images iteratively reconstructed with the weighting function have increased temporal resolution relative to images iteratively reconstructed without the weighting function.

6. The image reconstruction method of claim 1, wherein the angular weighting function is an angle-dependent weighting in which a higher weight is applied at a center view for a voxel, and lower weights are applied away from the center view.

7. The image reconstruction method of claim 6, wherein the higher weight has a value of 1 and the lower weights taper down to 0 for the views furthest from the center view.

8. The image reconstruction method of claim 1, wherein the one or more voxels for which the angular range is narrowed is limited to regions of motion.

9. An image reconstruction method, comprising the acts of:
   accessing scan data acquired using a computed tomography system, wherein the scan data comprises temporally offset scan data;
   computing a voxel-dependent angular weighting function corresponding to the scan data;
   using the respective weighting function to iteratively compute a set of images from the scan data, such that the angular range of the data contributing to each voxel is made more uniform and/or the angular range is narrowed for one or more voxels;

jointly reconstructing images generated based on the temporally offset scan data to generate one or more temporally offset images; and combining the temporally offset images using one or more of averaging, addition, weighted combination, or Fourier combination.

10. The image reconstruction method of claim 9, wherein the angular weighting function is view dependent.

11. The image reconstruction method of claim 9, wherein the angular weighting function is one of a trapezoidal weighting function or a rectangular weighting function.

12. The image reconstruction method of claim 9, wherein the scan data comprises helical scan data.

13. The image reconstruction method of claim 9, wherein the images iteratively reconstructed with the weighting function have increased temporal resolution relative to images iteratively reconstructed without the weighting function.

14. The image reconstruction method of claim 9, wherein the angular weighting function is an angle-dependent weighting in which a higher weight is applied at a center view for a voxel, and lower weights are applied away from the center view.

15. The image reconstruction method of claim 14, wherein the higher weight has a value of 1 and the lower weights taper down to 0 for the views furthest from the center view.

16. The image reconstruction method of claim 9, wherein the one or more voxels for which the angular range is narrowed is limited to regions of motion.

* * * * *